United States Patent [19]

Ersek et al.

[11] Patent Number: 5,624,419
[45] Date of Patent: Apr. 29, 1997

[54] CLOSEABLE, DISPOSABLE WOUND CARE SYSTEM

[76] Inventors: Robert A. Ersek, 62 Pascal, Austin, Tex. 78746; Arthur A. Beisang, 5009 Lake Ave., Unit 304, White Bear Lake, Minn. 55110

[21] Appl. No.: 427,671
[22] Filed: Apr. 24, 1995
[51] Int. Cl.$^6$ .............. A61F 5/44; A61F 13/00; A61B 19/00; A61M 1/00
[52] U.S. Cl. .............. 604/355; 604/357; 604/317; 604/304
[58] Field of Search .............. 604/278, 332, 604/335, 327, 307, 334, 277, 311, 304–306, 310; 383/61, 84, 85, 88, 98, 30–31; 128/846–847; 206/813

[56] References Cited

U.S. PATENT DOCUMENTS

| | | | |
|---|---|---|---|
| 2,815,024 | 12/1957 | Johnson | 604/311 |
| 3,142,436 | 7/1964 | Heigl | 383/30 |
| 3,910,274 | 10/1975 | Nolan | 604/277 |
| 4,084,590 | 4/1978 | Caraway et al. | 604/335 |
| 4,795,435 | 1/1989 | Steer | 604/332 |
| 4,969,880 | 11/1990 | Zamierowski | 604/305 |
| 5,048,692 | 9/1991 | Handler et al. | 383/85 |
| 5,248,307 | 9/1993 | Sokoloff | 604/332 |

*Primary Examiner*—John G. Weiss
*Assistant Examiner*—David J. Cho
*Attorney, Agent, or Firm*—Haugen and Nikolai, P.A.

[57] ABSTRACT

A receptacle for controlling and containing irrigation fluids administered to clean and irrigate a wound on a patient's body. The receptacle comprises a thin flexible film selected from the group consisting of polyethylene and polyvinyl chloride, and having an adhesive portion for sealing to the patient. The receptacle is in the form of a bag member and is utilized for retaining fluids along with a spraying or irrigation member, thereby enabling the wound irrigation procedure to be carried out in a closed system, and wherein upon completion of the procedure, the receptacle may be completely sealed and disposed of in an appropriate manner so as to avoid cross-contamination from a patient being treated to another person such as a health care professional or another patient.

11 Claims, 5 Drawing Sheets

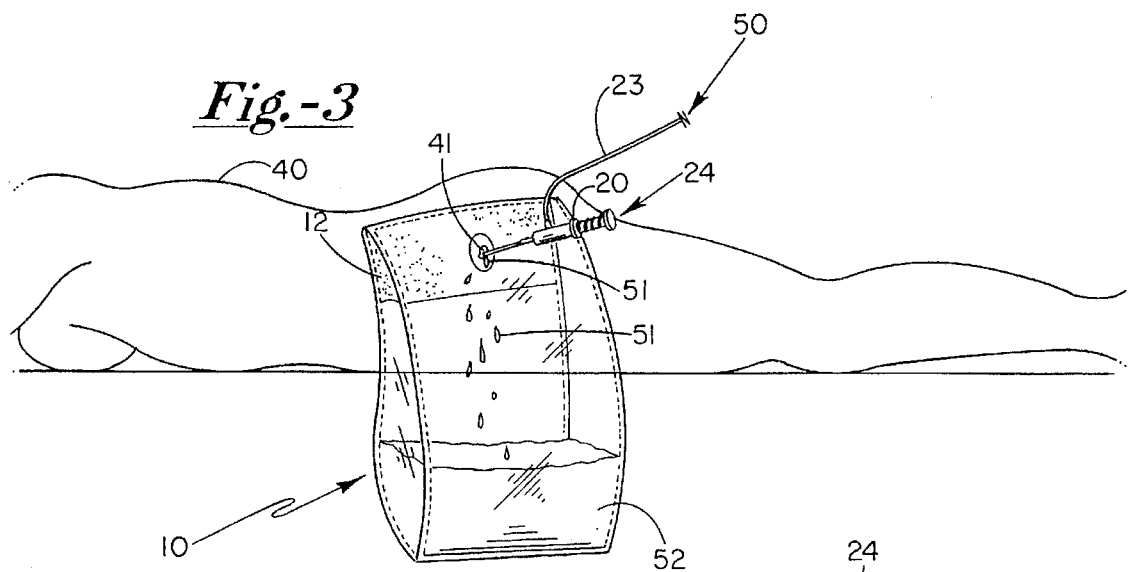
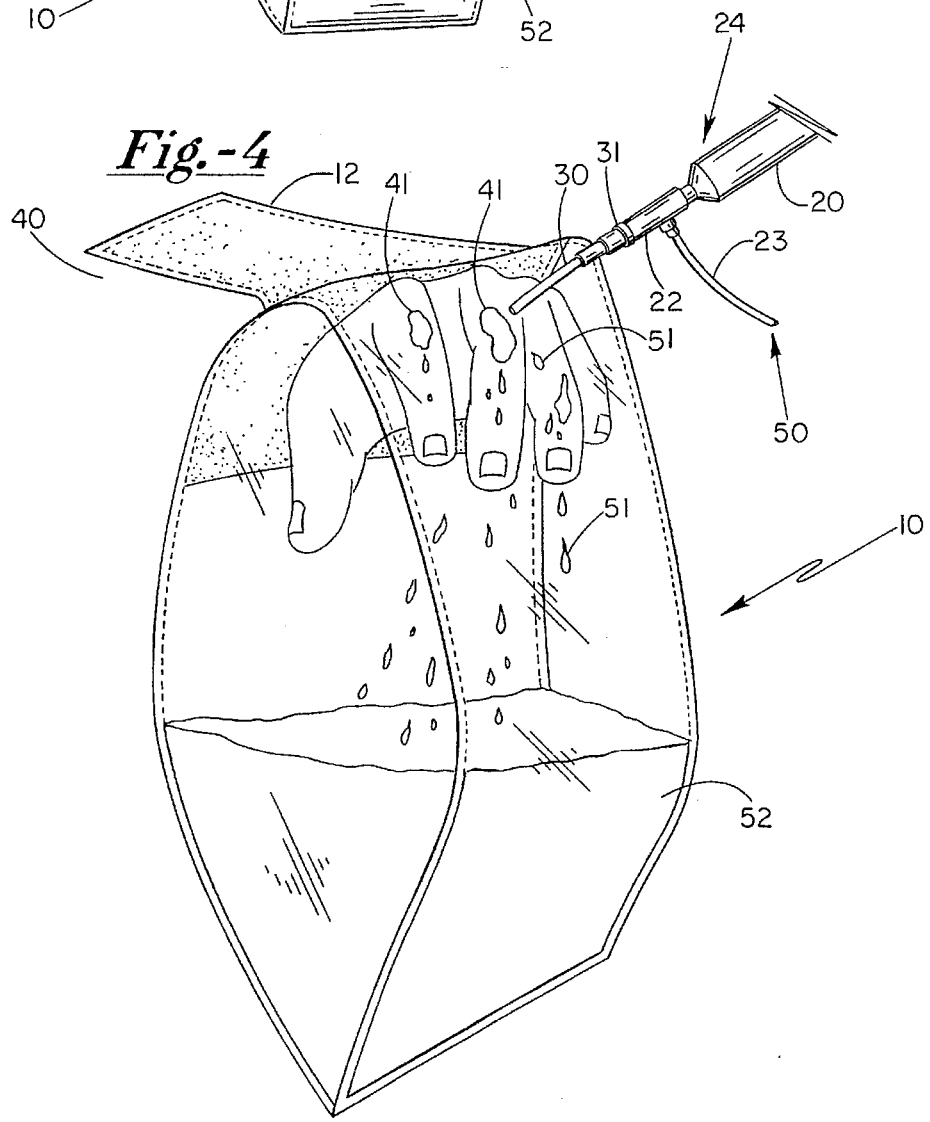

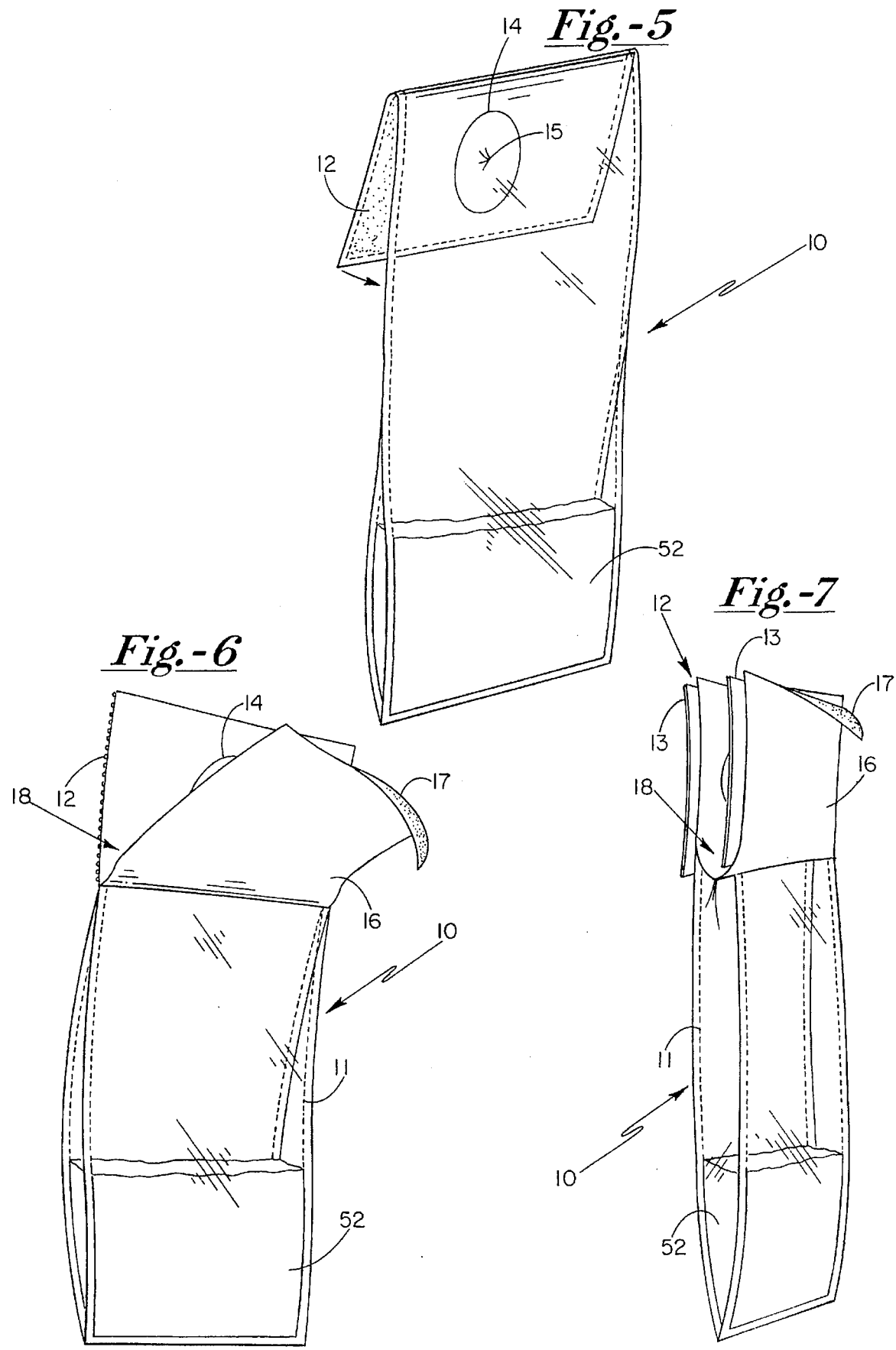

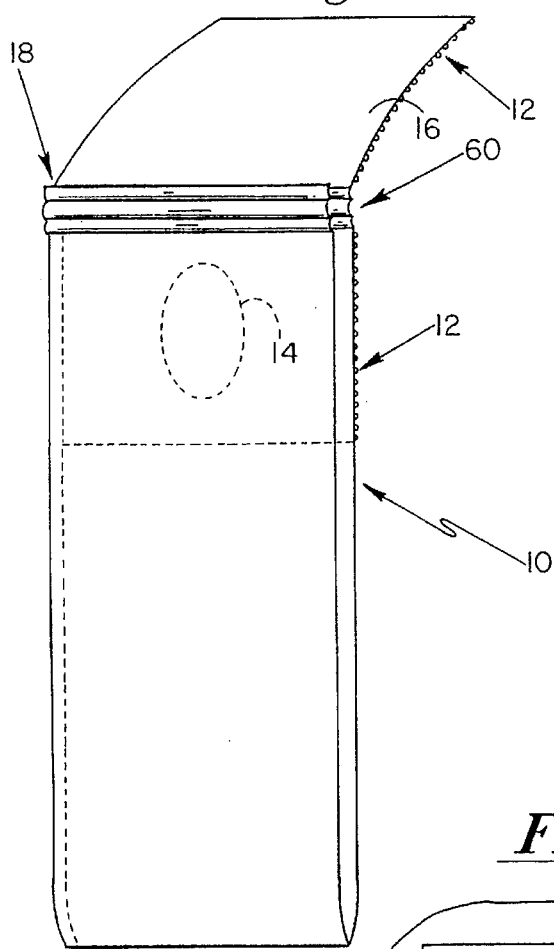
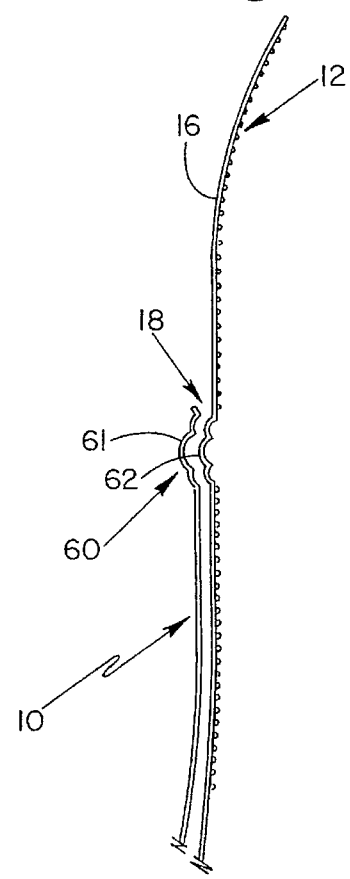
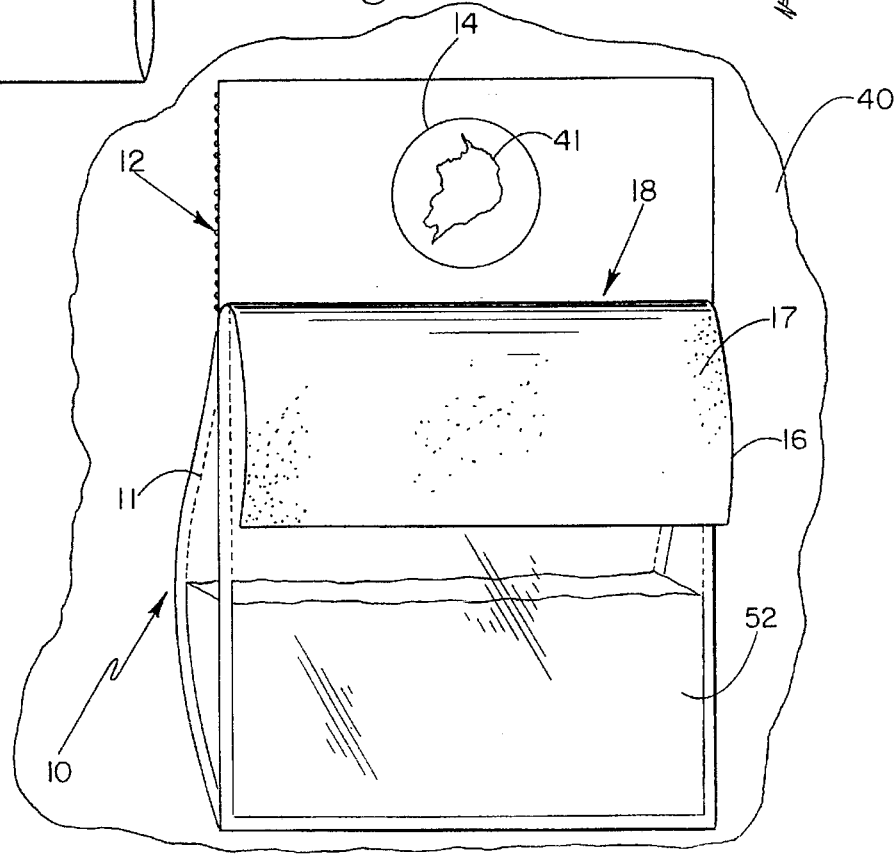

5,624,419

CLOSEABLE, DISPOSABLE WOUND CARE SYSTEM

BACKGROUND OF THE INVENTION

The present invention relates to receptacles, and more particularly, to receptacles used in the collecting, transporting, storing and disposing of fluids used in the medical field for cleaning and irrigation of acute and chronic wounds on the bodies of patients.

The present medical practice is typically to wash or irrigate wounds with a stream of fluid. Such fluids are normally of sterile, normal saline, soap and water, a variety of povidone/iodine and/or other antiseptic, antibiotic, or anesthetic solutions. In the present practice, a stream of flow is directed to the wound from an arrangement comprising a standard medical type syringe or IV tubing. This arrangement may or may not have a stop cock attached thereto, and may be driven by a powered member in the form of a hydraulic system commonly referred to as a water pik. In the past, the irrigating fluid would be splashed onto the wound surface with a moderate amount of force sufficient to dislodge dirt, debris, bacteria, or dead tissue. In this procedure, some fluid would ricochet from the wound surface and drip either to an open waiting bag, or onto some absorbent cotton bandages. At the completion of the procedure, the cotton bandages would be disposed of by placing them within a bacterial and viral-proof bag usually consisting of polyethylene or other suitable non-porous or substantially impermeable film and disposed of in a safe and sterile manner. The advent of blood-borne diseases that can be transmitted by the transfer of body fluids from a patient to a health care professional or to another patient via contaminated airborne particles (fomites) makes a closed system for such irrigation procedures imperative. Further, OSHA (Occupational Safety and Health Act of 1970) 29CF§ 1910.1030, requires universal precautions since all body fluids are to be considered potentially infectious. As such, they are characterized as regulated waste and must be placed in a closeable container.

SUMMARY OF THE INVENTION

In one typical configuration, the apparatus of the present invention consists of a bag or enclosure of thin plastic film such as polyethylene which is inherently heat sealable and having an outer perimeter that is welded along a continuous bead, and with a portion of the bag having an adhesive surface protected by a glazed paper to accommodate shipping and handling. A single hole is provided in the bag along the adhesive surface. In use, an irrigation or spraying member is passed through the hole and a source of irrigation fluid pressed through the film opposite said hole, so that attachment of the spraying member to the irrigation fluid source would form a reasonably sound seal. The gasket between the two members is formed from the perforated wall of the receptacle itself. After assembly, the protective glazed paper is peeled from the adhesive surface and the adhesive surface placed against an uninjured area or zone of the patient's body in such a way as to create a seal around and isolate the wound. The size of the fenestration may be increased by simply extending the fenestration by cutting a portion thereof, so that the hole would be slightly larger than the wound. After sealing to the surface of the skin of the patient, irrigation and spraying can commence with any ricocheting fluid or after-spray being retained within the receptacle member and collected by gravity at the bottom. After irrigation is complete, the receptacle member is separated from the patient. If the irrigation system were undertaken using a simple disposable tubing member, it is placed within the receptacle through the wound hole and thereafter the adhesive portion is folded over to adhere to the receptacle wall in such a way as to create a complete seal with the original hole being completely isolated. In this way, the entire contents of the receptacle remain isolated and sealed within the container for safe and sterile transport to appropriate disposal and incineration.

Alternatively, and in another configuration, the device consists of a bag member with an adhesive means covering a portion of the surface, and with a protective glazed paper over the adhesive for shipping and handling. In approximately the middle of this adhesive portion, a fenestration or a window is created by partial perforation of the glazed paper adhesive and the receptacle member to permit ease of removal at the time of use. In this configuration, instead of having the welding bead formed along the entire perimeter, a portion is left unwelded. The enclosure is then open mouthed, such as a common bag, but a sealable means is provided adjacent the opening so that, in this configuration, the device can be adherent to the skin surface around a wound. The opening gives ready access to the wound for suturing, disinfecting, irrigation, or otherwise treating the wound. Items such as used sutures, bandages, dressings and irrigation fluid are then collected in the receptacle portion and after completion of the suturing and/or irrigation process, the mouth of the bag may be sealably closed.

Therefore, it is a primary object of the present invention to provide an improved device which functions as a closed wound irrigation system and sealable fluid retaining receptacle to prevent cross-contamination from a patient being treated to another person.

It is yet a further object of the present invention to provide an improved wound irrigation system fabricated from a pair of flexible wall film members, heat sealed or otherwise welded about their periphery, having an adhesive surface with a hole therein to allow the attachment of an irrigation system, with the irrigation system being a simple intravenous fluid tubing member and stop cock or needle, a simple irrigating syringe, or a syringe with a renewable source of irrigating fluid, or a hydraulic or pneumatic mechanically or electrically operated pumping system.

It is yet another object of the invention to provide a single receptacle that is acceptable for virtually all routine wound irrigations.

Still a further object of the invention is a provision of a receptacle that is closable and disposable but not susceptible to breakage.

It is yet a further object of the invention to provide a receptacle that is easily hermetically sealed to avoid leaking and contamination.

Still an additional object of the present invention is to provide a receptacle that comprises a sealable, closeable, attachable receptacle means having an opened end to allow access to the wound for debridement, suture, or other wound care such that following such care, an irrigation system may be attached to the wall of a device having a sealable means to allow all of the debris of the suture debridement and irrigation collected in the receptacle member and sealed for appropriate disposal and decontamination.

It is yet another object of the present invention to provide a labeling identification system for identifying and disposing of certain types of medical waste.

Various other objects and advantages will appear from the following description of several embodiments of the invention, and the most novel features will be particularly pointed out hereinafter in connection with the appended claims.

IN THE DRAWINGS

The invention will be described in greater detail with reference to the accompanying drawings, wherein:

FIG. 3 is a perspective view of the invention in use with the assembled irrigation source here with the entire device attached adhesively to the patient (40) via an adhesive patient surface (12) of receptacle (10);

FIG. 4 is a perspective view similar to FIG. 3 wherein the wounded hand of patient (40) is completely placed within the receptacle (10);

FIG. 5 is a perspective view of the invention after use as the adhesive patient surface (12) is folded over to seal the fenestration (14);

FIG. 6 is a perspective view of an alternate embodiment of the invention having a receptacle (10) with an opening (18) for capturing spent irrigation fluid (52) and which is capable of being sealably closed with closeable flap member (16);

FIG. 7 is a perspective view of the device depicted in FIG. 6 with a protective glaze paper (13) in place over adhesive patient surface (12) and adhesive surface (17) of closeable flap member (16) as it might be just prior to use;

FIG. 8 is a perspective view of another embodiment of the invention having an interdigitating closeable lock (60) such as is commonly found in a zip-lock bag, for selectively accessing the interior of the receptacle (10) through the opening (18) and having an additional flap member (16);

FIG. 9 is a cross-sectional view of the device depicted in FIG. 8 showing the interdigitation of the closeable lock (60).

FIG. 10 is a perspective view of the embodiment depicted in FIG. 6 with the flap member (16) fully open, thereby providing access to the wound (41) through the fenestration (14);

DESCRIPTION OF THE PREFERRED EMBODIMENTS

Figure 1:
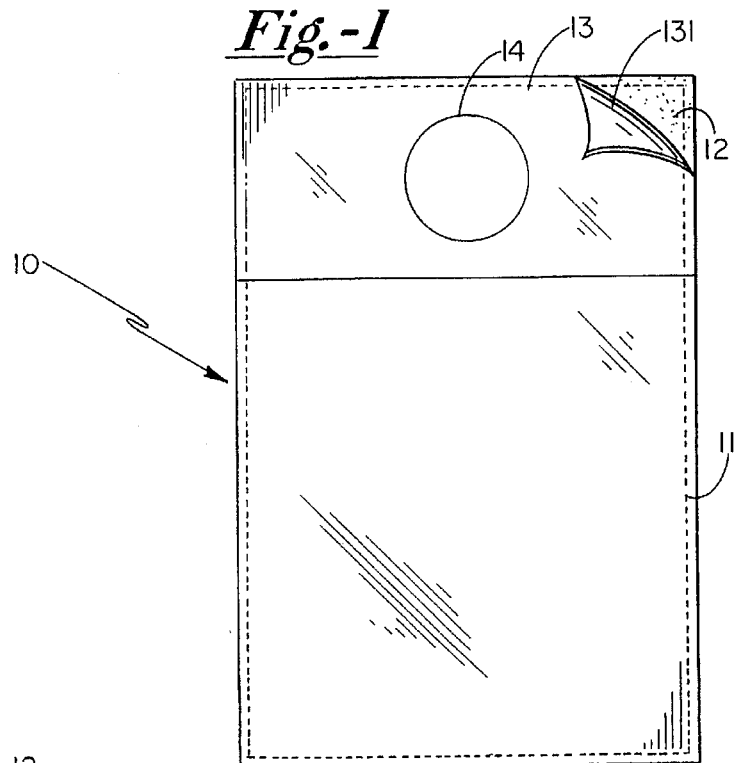
FIG. 1 is a perspective view of a receptacle embodying the present invention.

In accordance with the preferred embodiment of the present invention, and with particular attention being directed to FIGS. 1 and 5, there is illustrated a receptacle generally indicated at (10), constructed of film or other flexible sheet-like material, preferably polyethylene. Typically, polyethylene film is used having a thickness of between one-half and two mils, with one mil polyethylene being generally preferred. The receptacle (10) is heat welded or otherwise joined at its periphery (11) to form a continuous seal. An adhesive material (12) is disposed along an upper periphery of one surface of the receptacle (10) for adhering the receptacle (10) to a patient. This surface, referred to hereinafter as the adhesive patient surface (12), is protected and covered prior to use by a sheet of glazed paper (13). A single fenestration or hole (14) is formed through the receptacle (10) within the adhesive patient surface (12). In FIG. 1, the protective glazed paper (13) is shown partially peeled back at the corner (see peeled back portion (131)) exposing the adhesive patient surface (12). In FIG. 5, spent irrigation fluid (52) is shown at the bottom portion of the receptacle (10) and with the adhesive patient surface (12) being placed in juxtaposition to the outer surface of the receptacle (10) at the end opposite the reservoir fluid (52). This permits the fenestration (14) and the irrigator puncture site (15) to be completely sealed, thereby preventing leakage or escape of the fluids (52) and other items contained therein.

Figure 2:
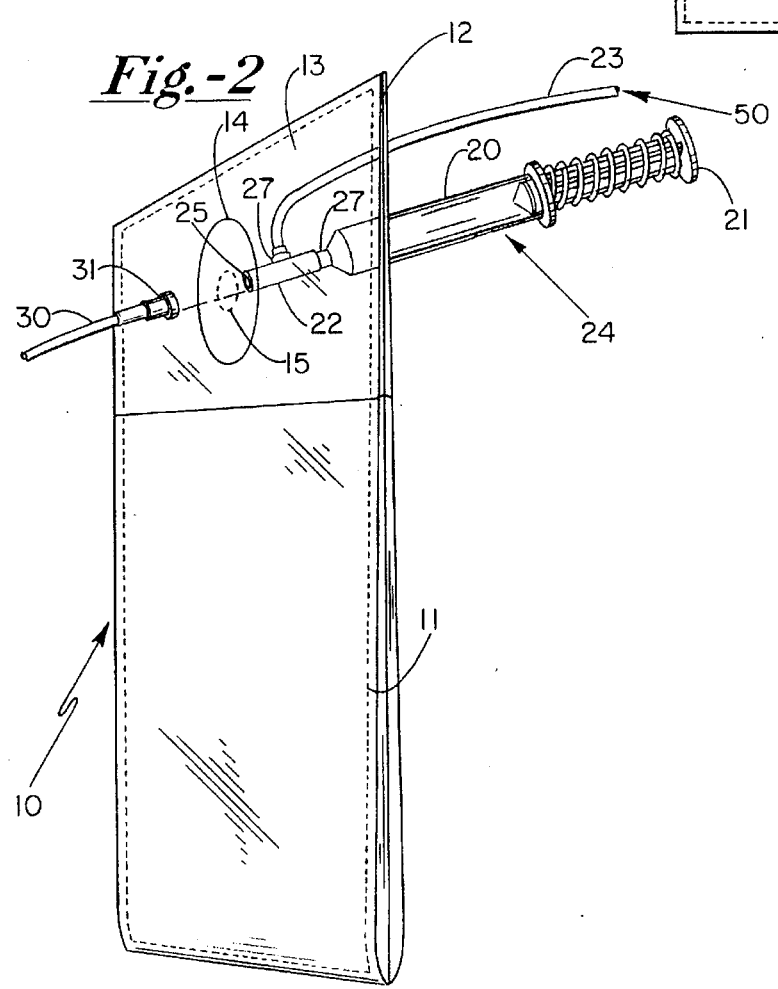
FIG. 2 is a perspective view of the invention of FIG. 1 with an irrigation source shown in an exploded view prior to assembly.

In FIG. 2, the receptacle member (10) is shown with an irrigation source, shown generally at (24), comprising an irrigation spray nozzle (30) in line to be attached to an irrigation source lock (22) having a plurality of inlet ports (27) and an outlet port (25). As shown in FIG. 2, the inlet ports (27) are coupled to a syringe (20) and a fluid supply tube (23), while the outlet port (25) is in line to be attached to the irrigation spray nozzle (30). The irrigation source lock (22) may be any one of several commercially available stop cocks or syringe fittings. In use, the outlet port (25) of the irrigation source lock (22) is piercingly forced through the wall of the receptacle (10) opposite the fenestration (14) as at (15) to interlock with a flange member (31) of the spray nozzle (30) such that the stretched wall of the receptacle (10) serves as a gasket. The fluid supply tube (23) is disposed to provide fluid communication between the irrigation source lock (22) and a fluid source (not shown). The fluid source may be a simple sterile irrigation fluid bag or bottle which may traverse under the influence of gravity through the irrigation source lock (22) into the spray nozzle (30) to be sprayed upon the wound (not shown). Alternatively, the fluid source may simply be the syringe (20) having a plunger mechanism (21) that can be manually or mechanically operated to provide the necessary and appropriate force to spray the irrigating fluid through the spray nozzle (30).

With attention now being directed to FIG. 3, the assembled wound irrigation system as illustrated is adherent to a patient (40) for a wound (41) on the patient's hip.

With attention now being directed to FIG. 4, the alternative preferred embodiment of the invention illustrated is shown in place with the adhesive patient surface (12) being disposed adjacent the patient's arm (40). In this case, the adhesive patient surface (12) encompasses the entire wrist wherein the hand has been placed through the fenestration (14). The irrigation fluid, shown entering the fluid supply tube (23) as at (50) passes through the outlet port (not shown) of the irrigation source lock (22) and further through the irrigation spray nozzle (30) after being directed between the fluid supply tube (23) and the syringe (20) by the irrigation source lock (22). In the preferred embodiments shown in FIGS. 2–4, the irrigation source lock (22) is a commercially available fitting for attachment to the syringe (20) and the fluid supply tube (23). The irrigation source lock (22) is thus capable of directing the fluid from the fluid source (not shown) into the syringe (20) responsive to the outward movement of the syringe plunger (21), as well as directing the fluid within the syringe (20) out the nozzle (30) responsive to the inward movement of the syringe plunger (21). After coming in contact with the wound (41), the irrigation fluid is sprayed as droplets (51) and collected at the lower periphery of the receptacle (10), as shown at (52).

In actual operation and in carrying out the procedure with the use of the present invention, the protective releasable glazed paper member or film (13) is removed from the adhesive patient surface (12), with that portion of the receptacle (10) being placed into an appropriate area of the patient surrounding the wound (41). The size or length of fenestration (14) may be adjusted or otherwise modified to accommodate the configuration of the wound (41). After use, the receptacle (10) is removed from the patient (40) and folded in such a way that the adhesive patient surface (12) is removed from the skin of the patient and then doubled over and attached to the wall of the receptacle (10) so that the fenestration (14) and puncture hole (15) are isolated and sealed from the inner portion of the receptacle (10), thereby isolating its contents (52).

With attention now being directed to FIG. 6 of the drawings, shown is an alternate embodiment of the present invention, wherein the receptacle (10) is provided with heat sealed or welded seams (11) that extend a predetermined distance along the lateral edges of the receptacle (10) to provide an opening, shown generally at (18), capable of receiving spent irrigation fluid or debris (52) disposed and retained in the bottom of the receptacle (10). In this embodiment, flap member (16) has an adhesive surface (17) which faces the fenestration (14). In practice, releasable glazed paper or film (13) is disposed on the adhesive surface (17) for isolation and protection until after use. At that time, adhesive patient surface (12) may be separated from a patient and rolled into the opening (18) of the receptacle (10). When the protective glazed paper (13) is removed from the adhesive surface (17), the flap member (16) may be folded down to be sealably and closeably attached to the opposite side of the receptacle (10), thereby isolating and retaining the contents (52) therein.

With attention now being directed to FIG. 7, shown is a side view of the alternative embodiment in FIG. 6 prior to use with the glazed releasable paper (13) remaining disposed on both the adhesive patient surface (12) and the adhesive surface (17) of flap member (16). The sealable, closeable opening (18) is illustrated here in its open position.

With attention now being directed to FIGS. 8 and 9 of the drawings, shown is another preferred embodiment of the present invention, wherein the adhesive patient surface (12) extends along a portion of the receptacle (10) surrounding the fenestration (14) and further along the underside of a flap member (16) that extends away from the top edge of the receptacle (10). Following use, this flap member (16) may be folded downwardly to cover the lower portion of the adhesive patient surface (12), as shown in dotted lines below the fenestration (14), to thereby create a seal over the fenestration (14). An interdigitating and mutually coupling closeable lock (60) is provided so that the contents of the receptacle (10) may be sealed and isolated by obstructing the opening (18). Such interdigitating lock means are, of course, commercially available and, as shown in FIG. 9, provide selective access to the interior of the receptacle (10) and, hence, the wound via the coupling relationship between an outer engaging portion (61) and an inner engaging portion (62) of the interdigitating lock (60) for suturing, cleaning, and the like.

With attention now being directed to FIG. 10 of the drawings, there is illustrated the device of FIG. 6 during use, wherein the adhesive patient surface (12) allows the receptacle (10) to be attached to the surface of the skin of the patient (40), giving full and clear access to the wound (41) through the fenestration (14). As illustrated herein, flap member (16) may be folded downwardly to give full and clear access to the wound (41) for suturing, debridement, and/or other indicated wound care. After use and collection of all wound related refuse (52), protective glazed paper (not shown) is removed from a covering relationship over the adhesive surface (17) of the flap member (16). The adhesive patient surface (12) is then peeled away from the patient, rolled upon itself and stuffed into the opening (18), so that the flap member (16) may be folded over onto the opposite surface of the receptacle (10), thereby completely sealing the contents (52) and the opening (18) of receptacle (10).

Figure 11:
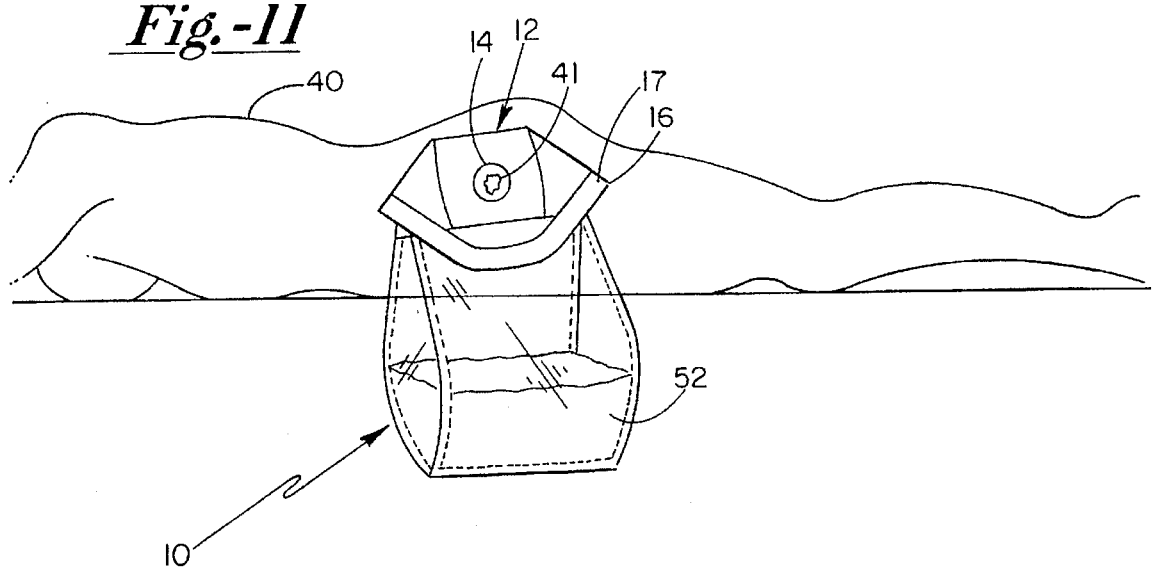
FIG. 11 is a perspective view of yet another embodiment of the present invention as attached to a patient (40).

With attention now being directed to FIG. 11, there is illustrated a perspective view of an alternative preferred embodiment of the present invention, with the receptacle (10) attached to a patient (40). In this embodiment, a sealable, closeable surface or flap member (16) is disclosed having an adhesive sealing surface (17) disposed thereon which, during use, is covered with a removable protective glazed paper (not shown). Following use, the adhesive patient surface (12) is folded upon itself and placed within the receptacle (10). The glazed paper (not shown) is then removed from the adhesive surface (17) of the flap member (16) so that the flap member (16) may be folded over to completely seal and isolate the contents (52).

Another feature of the invention is that it can be fabricated of a material such as, for example, vinyl, the surface of which can be modified to accept ink and thereby can be easily written upon so as to designate such information as the patient's name, source of the material, or bar code or other identifying means for tracking of medical waste as currently required in many jurisdictions. Other films, including polyethylene, may be treated so as to accept certain types of inks, and are, of course, commercially available.

It will be understood that variations, and various and other changes in the details, materials, steps and arrangements of parts which have been herein described and illustrated in order to explain the nature of the invention may be made by those skilled in the art within the principle and scope of the invention.

What is claimed is:

1. A receptacle for use in the collection, transportation, storage and disposal of contaminated wound fluids from a patient having a wound, comprising:

a moisture impermeable film container for receiving contaminated wound fluids, said container having opposing first and second generally planar surfaces, generally parallel opposing lateral edges, an upper periphery, and a lower periphery;

a first closeable opening formed in said first generally planar surface proximates said upper periphery;

a continuous adhesive film layer disposed on said first generally planar surface proximate said first closeable opening defining an adhesive patient surface; and a releasable protective film member removably secured to said adhesive patient surface to cover said adhesive film layer prior to use;

wherein, during use, said protective film member is removed from said adhesive patient surface to avail said adhesive film lawyer for securing said container to said patient, and said adhesive patient surface is positioned on said patient such that said first closeable opening exposes said wound of said patient; and wherein, following use, said adhesive patient surface is removed from said patient and folded to sealably close said first closeable opening.

2. The receptacle as defined in claim 1 and further, comprising:

a second closeable opening formed between said opposing lateral edges proximate said upper periphery of said container for providing access to said first closeable opening; and a flap member having an adhesive surface extending outwardly away from said second closeable opening.

3. The receptacle as described in claim 2 wherein said flap member is capable of being folded such that said adhesive surface of said flap member forms a sealed closure about said second closeable opening.

4. The receptacle as described in claim 2 wherein a pair of mutually engaging interdigitated ribs are disposed between said opposing lateral edges proximate said second closeable opening so as to provide selective access to the contents of said container.

5. The receptacle as defined in claim 4 and further, wherein said first closeable opening is disposed within said container such that the mutually engaging relationship between said interdigitating ribs provides selective access to said first closable opening, and wherein, after use, said flap member is capable of being folded to sealably close said first closeable opening.

6. A receptacle for use in the collection, transportation, storage and disposal of contaminated wound fluids from a patient having a wound, comprising:

a moisture impermeable film container for receiving contaminated wound fluids, said container having opposing first and second generally planar surfaces, generally parallel opposing lateral edges, an upper periphery, and a lower periphery;

an irrigation source coupled to said second generally planar surface of said container for directing an irrigation fluid toward said wound of said patient;

a first closeable opening formed in said first generally planar surface proximate said upper periphery;

a continuous adhesive film layer disposed on said first generally planar surface proximate said first closeable opening defining an adhesive patient surface; and a releasable protective film member removably secured to said adhesive patient surface to cover said adhesive film layer prior to use;

wherein, during use, said protective film member is removed from said adhesive patient surface to avail said adhesive film layer for securing said container to said patient, said adhesive patient surface is positioned on said patient such that said first closeable opening exposes said wound of said patient; and wherein, following use, said adhesive patient surface is removed from said patient and folded to sealably close said first closeable opening.

7. The receptacle as set forth in claim 6 and further, wherein said irrigation source comprises:

an irrigation source lock having a plurality of inlet ports and an outlet port;

a syringe coupled to one of said plurality of inlet ports of said irrigation source lock, said syringe having an internally disposed and slidable plunger for drawing said irrigation fluid into said syringe and for forcing said irrigation fluid out of said syringe;

a fluid supply tube coupled to another of said plurality of inlet ports of said irrigation source lock, said fluid supply tube capable of transporting said irrigation fluid from a fluid source to said irrigation source lock;

a spray nozzle having a flange member capable of being connected to said outlet port of said irrigation source lock for directing the outflow of said irrigation fluid from said irrigation source lock; and wherein, during use, said outlet port of said irrigation source lock is piercingly forced through said second generally planar surface and engagingly coupled to said flange member of said spray nozzle such that said second generally planar surface forms a gasket between said irrigation source lock and said spray nozzle.

8. The receptacle as set forth in claim 7 and further, wherein irrigation source lock cooperates with said syringe responsive to the slidable position of said plunger such that said irrigation source lock permits said irrigation fluid to flow from said fluid supply tube into said syringe during an outward sliding motion of said plunger relative to said syringe, and such that said irrigation source lock permits said irrigation fluid to flow through said outlet port during an inward sliding motion of said plunger relative to said syringe.

9. The receptacle as described in claim 6 wherein said irrigation source comprises a spray nozzle coupled to a mechanically operated source of irrigation fluid.

10. The receptacle as set forth in claim 3 and further, wherein, after use, said adhesive patient surface is capable of being folded and received within said second closeable opening, and wherein said flap member is thereafter capable of being folded over said second closeable opening to closeably seal said adhesive patient surface and said contaminated wound fluids within said container.

11. The receptacle as set forth in claim 6 and further, wherein said irrigation source comprises:

an irrigation source lock comprising one of a syringe fitting and a bi-directional valve;

a spray nozzle capable of being connected to said irrigation source lock for directing said irrigation fluid from said irrigation source lock to said wound of said patient; and wherein said irrigation source lock and said spray nozzle are coupled together such that said second generally planar surface forms a gasket between said irrigation source lock and said spray nozzle.

* * * * *

UNITED STATES PATENT AND TRADEMARK OFFICE
CERTIFICATE OF CORRECTION

PATENT NO. : 5,624,419
DATED : April 29, 1997
INVENTOR(S) : Robert A. Ersek et al.

It is certified that error appears in the above-indentified patent and that said Letters Patent is hereby corrected as shown below:

Column 6, line 43, "proximates" should read -- proximate --
Line 52, "lawyer" should read -- layer --.

Column 8, line 19, after"wherein" insert -- said --.

Signed and Sealed this

Fifteenth Day of July, 1997

Attest:

BRUCE LEHMAN

*Attesting Officer*　　　　Commissioner of Patents and Trademarks